United States Patent
Stayman et al.

(10) Patent No.: US 11,724,129 B2
(45) Date of Patent: Aug. 15, 2023

(54) METHOD FOR OPTIMIZING RADIATION BEAM INTENSITY PROFILE SHAPE USING DUAL MULTIPLE APERTURE DEVICES

(71) Applicants: THE JOHNS HOPKINS UNIVERSITY, Baltimore, MD (US); Koninklijke Philips NV., Eindhoven (NL)

(72) Inventors: Joseph Webster Stayman, Baltimore, MD (US); Aswin John Mathews, Baltimore, MD (US); Reuven Levinson, Haifa (IL)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 74 days.

(21) Appl. No.: 17/545,030

(22) Filed: Dec. 8, 2021

(65) Prior Publication Data
US 2022/0088417 A1   Mar. 24, 2022

Related U.S. Application Data

(63) Continuation of application No. 15/639,044, filed on Jun. 30, 2017, now abandoned.
(Continued)

(51) Int. Cl.
*A61N 5/10* (2006.01)
*G01N 23/00* (2006.01)
*G21K 1/10* (2006.01)

(52) U.S. Cl.
CPC ........... *A61N 5/1077* (2013.01); *G01N 23/00* (2013.01); *G21K 1/10* (2013.01); *G01N 2223/316* (2013.01)

(58) Field of Classification Search
None
See application file for complete search history.

(56) References Cited

U.S. PATENT DOCUMENTS

| | | | |
|---|---|---|---|
| 5,461,653 | A | 10/1995 | Parker |
| 9,263,160 | B2 | 2/2016 | Kang et al. |

(Continued)

FOREIGN PATENT DOCUMENTS

WO   2014087305 A1   6/2014

OTHER PUBLICATIONS

Matthews et al., "Design of dual multiple aperture devices for dynamical fluence field modulated CT." Conf Proc Int Conf Image Form Xray Comput Tomogr., (2016), 2016, pp. 29-32.
(Continued)

*Primary Examiner* — David P Porta
*Assistant Examiner* — Mamadou Faye
(74) *Attorney, Agent, or Firm* — MH2 Technology Law Group LLP (57) ABSTRACT

The present invention is directed to multiple aperture devices (MADs) for beam shaping in x-ray imaging. Two or more of these binary filters can be placed in an x-ray beam in series to permit a large number of x-ray fluence profiles. However, the relationship between particular MAD designs and the achievable fluence patterns is complex. The present invention includes mathematical and physical models that are used within an optimization framework to find optimal MAD designs. Specifically, given a set of target fluence patterns, the present invention finds, for example, a dual MAD design that is a "best fit" in generating the desired fluence patterns. This process provides a solution for both the design of MAD filters as well as the control actuation that is required (relative motion between MADs) that needs to be specified as part of the operation of a MAD-based fluence field modulation system.

20 Claims, 10 Drawing Sheets

Related U.S. Application Data (60) Provisional application No. 62/356,690, filed on Jun. 30, 2016.

(56) References Cited

U.S. PATENT DOCUMENTS

| | | | |
|---|---|---|---|
| 2010/0119033 A1 | 5/2010 | Li et al. | |
| 2010/0246764 A1* | 9/2010 | Itoh | G21K 7/00 378/150 |
| 2013/0039472 A1* | 2/2013 | Morton | G01V 5/0033 378/88 |
| 2015/0100290 A1 | 4/2015 | Falt et al. | |
| 2015/0305698 A1 | 10/2015 | Katchalski et al. | |

OTHER PUBLICATIONS

Bartolac et al., "Fluence field optimization for noise and dose objectives in CT." Med. Phys., (2011), 38 (Suppl 1), p. S2.

Hasegawa et al. Selective Exposure Radiography using digitally formed x-ray beam attenuators. Proc. SPIE., (1983), 0419, pp. 282-288.

Szczykutowicz et al., "Design of a digital beam attenuation system for computed tomography. Part II. Performance study and initial results." Med. Phys., (2013), 40 (2), 021906.

Hsieh et al., "The feasibility of a piecewise-linear dynamic bowtie filter." Med. Phys., (2013), 40 (3), 031910.

Liu et al., "Dynamic bowtie filter for cone-beam/multi-slice CT." PLoS One., (2014), 9 (7), pp. 1-10.

Shunhavanich et al., "Fluid-filled dynamic bowtie filter: a feasibility study." Proceedings of SPIE, (2015), 9412, 94121L.

Szczykutowicz et al. Fluid Dynamic Bowtie Attenuators., Proc. SPIE, (2015), 9412, pp. 1-7.

Stayman et al. Fluence-Field Modulated X-ray CT using Multiple Aperture Devices. Proc SPIE Int Soc Opt Eng., (2016), 9783, 97890X.

Siewerdsen et al. Spektr: A computational tool for x-ray spectral analysis and imaging system optimization. Med. Phys., (2004), 31 (11), p. 3057.

Hsieh et al. Algorithms for optimizing CT fluence control. Proc SPIE., (2014), 9033, 9033M.

Gang et al. Task-driven tube current modulation and regularization design in computed tomography with penalized-likelihood reconstruction. SPIE Medical Imaging., (2016), 9783, 978324.

\* cited by examiner

METHOD FOR OPTIMIZING RADIATION BEAM INTENSITY PROFILE SHAPE USING DUAL MULTIPLE APERTURE DEVICES

CROSS REFERENCE TO RELATED APPLICATION

This application is a continuation of U.S. application Ser. No. 15/639,044 filed Jun. 30, 2017, which claims the benefit of U.S. Provisional Patent Application No. 62/356,690 filed on Jun. 30, 2016, all of which are incorporated by reference herein in their entirety.

GOVERNMENT RIGHTS

This invention was made with government support under 5U1EB018758 awarded by the National Institutes of Health. The government has certain rights in the invention.

FIELD OF THE INVENTION

The present invention relates generally to medical imaging. More particularly, the present invention relates to a method for optimizing radiation beam intensity profile shape using dual multiple aperture devices.

BACKGROUND OF THE INVENTION

X-ray computed tomography has found widespread clinical utility; however, increasing concerns about the risks associated with ionizing radiation have driven the search for exposure reduction strategies. While many algorithmic strategies for producing better images at lower exposures have been developed, there has been relatively little research on innovative hardware-based dose reduction methods. Dose to an individual patient is naturally tied to the particular exposure settings of a CT scanner; however, finding minimum dose strategies is both complex due to the dependence on patient size, anatomical site, etc. and, currently, somewhat limited due to the relative inflexibility of modern CT scanners to control the distribution of x-rays used to image a patient.

Typical clinical scanners permit coarse control of the x-ray beam through exposure settings (tube current and voltage), and many systems have tube current modulation hardware that permits variation of exposure as a function of rotation angle and table position. Control of the spatial distribution of the x-ray beam is typically very limited and is achieved through the introduction of a bow-tie filter. Some systems allow selection from a small number (typically three or fewer) bow-tie filters based on patient size. Typical filters attenuate x-rays at large fan angles to achieve higher fluence levels in the center of the patient (where the attenuation is highest) and lower fluence at the edges (where attenuation is low). Unfortunately, such static beam shaping is limited and cannot account for variability in the width/size of the patient as a function of angle and table position. Similarly, static bow-tie filters can be sensitive to positioning since a well-centered patient is presumed.

Fluence-field modulated (FFM) CT is an area of active research that seeks strategies for dynamic modulation of the spatial distribution of the x-ray beam. Successful implementation of FFM-CT increases acquisition flexibility permitting dose reduction objectives as well as novel data collection strategies (e.g., region-of-interest scans). A number of different FFM strategies have been proposed including the use of heavy metal compounds on paper, digital beam attenuators, piece-wise linear dynamic bowties, and fluid filled attenuators. Due to the severe operational requirements within a CT scanner (e.g. limited space, high rotation speeds, accelerations, etc.), the design of dynamic FFM-CT is a challenge.

Accordingly, there is a need in the art for a method for a method for optimizing radiation beam intensity profile shape using dial multiple aperture devices.

SUMMARY OF THE INVENTION

The foregoing needs are met, to a great extent, by the present invention which provides a method for a device for beam shaping in imaging having two or more multiple aperture devices placed in series. Each of the multiple aperture devices have a design and each of the multiple aperture devices are configured to have motion relative to others of the multiple aperture devices. The design and the motion of the multiple aperture devices is predetermined to generate a predetermined fluence pattern.

In accordance with an aspect of the present invention, the design and relative motion are chosen using mathematical models. The design and relative motion can also be chosen using physical models. Alternately, the design and relative motion are chosen using mathematical and physical models. Alternately, the motion of the multiple aperture devices is chosen according to real time data from the imaging scanner. The predetermined fluence pattern is based on a single target object or a group of target objects. The multiple aperture device includes bars. Design characteristics take the form of thickness of each bar, position of each bar relative to one another, and the frequency of the bars.

In accordance with another aspect of the present invention, a method for beam shaping in imaging includes placing two or more multiple aperture devices in series. Each of the multiple aperture devices has a design and each of the multiple aperture devices are configured to have motion relative to others of the multiple aperture devices. The method also includes generating a fluence pattern.

In accordance with yet another aspect of the present invention, the method includes predetermining the design and the motion of the multiple aperture devices to generate a predetermined fluence pattern. The method further includes determining the motion of the multiple aperture devices on-the-fly to generate a fluence pattern. The method includes programing the design and relative motion with one chosen from a group of using mathematical models, physical models, or a combination of the two. The method includes basing the predetermined fluence pattern on a single target object. Alternately, the predetermine fluence pattern can be based on a group of target objects. The multiple aperture device can include bars. Design characteristics can take the form of thickness of each bar. Design characteristics take the form of position of each bar relative to one another. Design characteristics can also take the form of the frequency of the bars.

BRIEF DESCRIPTION OF THE DRAWING

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to multiple aperture devices (MADs) for beam shaping in x-ray imaging. Two or more of these binary filters can be placed in an x-ray beam in series to permit a large number of x-ray fluence profiles. However, the relationship between particular MAD designs and the achievable fluence patterns is complex. The present invention includes mathematical and physical models that are used within an optimization framework to find optimal MAD designs. Specifically, given a set of target fluence patterns, the present invention finds, for example, a dual MAD design that is a "best fit" in generating the desired fluence patterns. This process provides a solution for both the design of MAD filters as well as the control actuation that is required (relative motion between MADs) that needs to be specified as part of the operation of a MAD-based fluence field modulation system.

Figure 1:
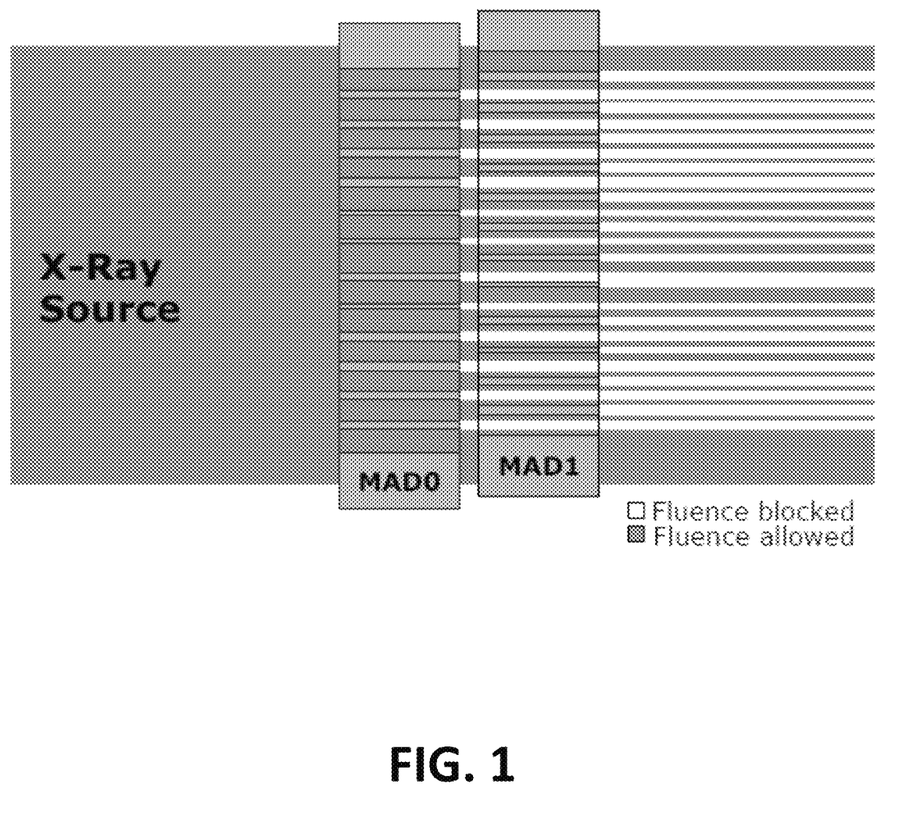
FIG. 1 illustrates a schematic diagram of fluence modulation using Dual MAD filters.

The conceptual operation of a MAD filter is illustrated in FIG. 1. FIG. 1 illustrates a schematic diagram of fluence modulation using Dual MAD filters. The device comprises thin bars of a highly attenuating material (e.g. tungsten) of varying widths and spacing. On a fine scale the MAD acts as a binary filter, either completely blocking or passing the X-ray beam using alternating bars and slots. In this fashion, one can concentrate the amount of x-rays spatially by varying the thickness of the blockers locally. The pitch (spacing between blockers) of the MAD device may be designed to minimize high-frequency patterns at the detector. For example, if the focal spot of the x-ray source is assumed to be a rectangle, the MAD pitch may be placed at the first null frequency associated with the focal spot blur MTF. In this fashion, the fine bar pattern of the MAD device is blurred out and is not visible at the detector. Desirable (lower frequency) spatial modulation associated with the variable bar width is still achievable.

A single fluence pattern can be obtained with a single MAD device. With multiple MADs in series, capable of moving with respect to each other, a range of fluence patterns can be obtained since it is the composition of two binary filters. Moreover, small relative displacement of the MADs with respect to each other can induce large changes in the fluence pattern. Because small actuations have a large effect on the x-ray distribution, speed and acceleration requirements can be reduced for device. Similarly, because these filters do not rely on variable attenuation using a low atomic number material, the filters can be made very thin and compact.

Figure 2:
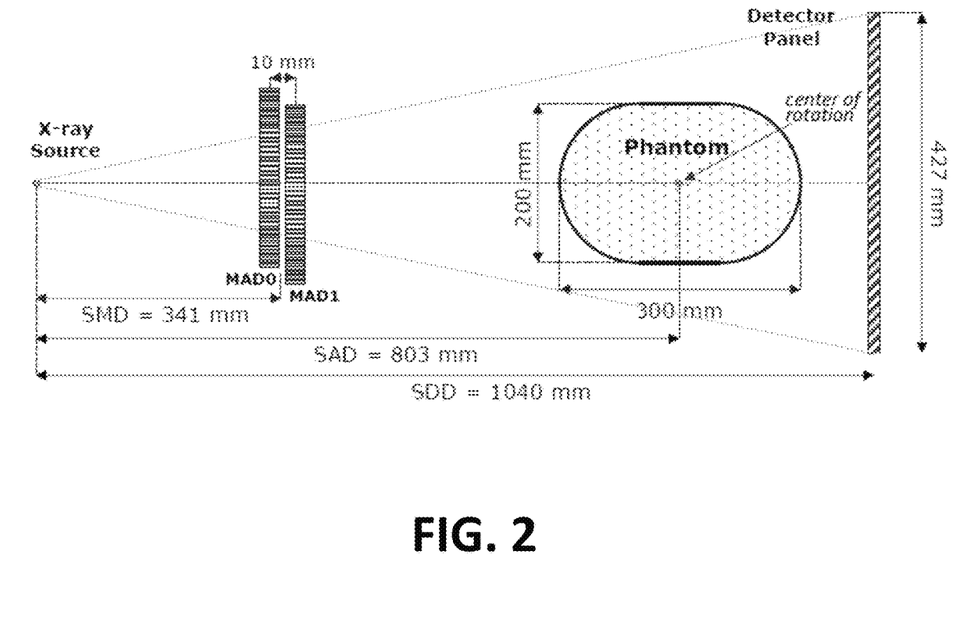
FIG. 2 illustrates a graphical view of simulated CT geometry and phantom.

Fluence optimization for a single target object is discussed as an example, herein; however, the approach may be extended to classes of objects. Specifically, the known object in the simulation study was chosen to be an anthropomorphic phantom body of uniform material (acrylic), as illustrated in FIG. 2. FIG. 2 illustrates a graphical view of simulated CT geometry and phantom. This digital phantom emulates commercially available physical phantoms (QRM GmbH, Morehendorf, Germany) that will be used in subsequent presentation of the invention.

The system geometry was chosen to emulate a CT scanner's source-to-detector distance and also geometry achievable in a flat-panel-based experimental test bench that is available for subsequent experiments. The exemplary implementation of the present invention includes 360 degree rotation, in steps of 0.5 degree. To create projection data for MAD design and analysis, a polyenergetic forward model and Spektr, a computational tool for x-ray spectral analysis, corresponding to a tube voltage of 100 kVp with additional filtration (2 mm of Al, 0.2 mm of Cu) were used. The model also includes fluence adjustments to accommodate divergent beam effects.

Figure 3:
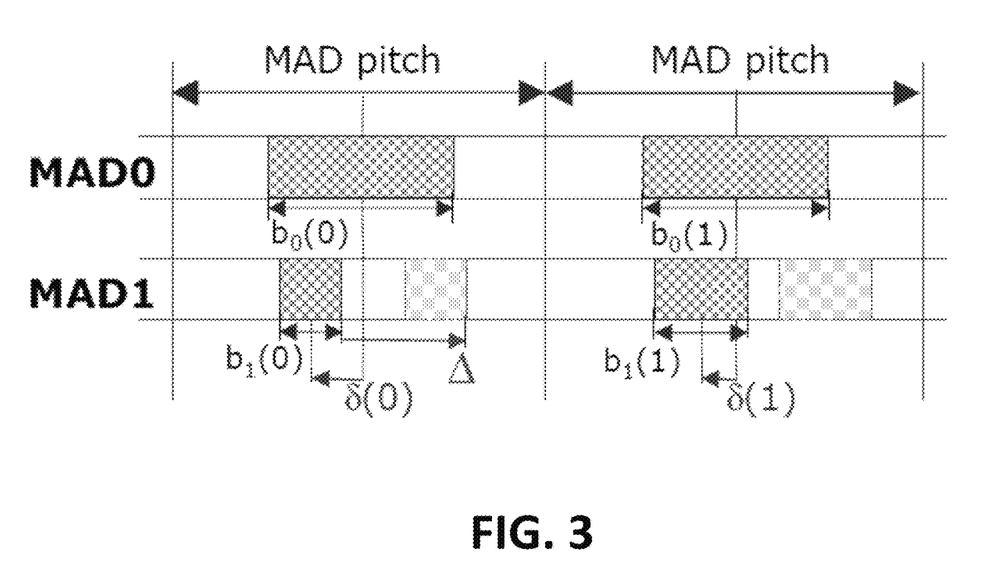
FIG. 3 illustrates a graphical view of parameterization of the MAD design.

In order to design a set of MAD filters, the location and dimensions of many MAD attributes must be specified. The elements of a dual MAD design are identified in the illustration in FIG. 3. FIG. 3 illustrates a graphical view of parameterization of the MAD design. Specifically, the free design parameters include: 1) $b_0(x)$, the thickness of each bar as a function of position in MAD0 that locally blocks X-rays; 2) $b_1(x)$, the analogous bar function for MAD1; 3) $\delta(x)$, a local offset function that specifies the position of individual bars in MAD1 relative to MAD0; and 4) the MAD pitch (e.g., the spacing interval between bars). The MAD pitch may be designed independently of other parameters based on the first null frequency of the focal spot, magnified to the MAD plane. For a rectangular focal spot size, $f_s$, the optimal MAD pitch is $$m = f_s \times \left(1 - \frac{SMD}{SDD}\right)$$

For nonrectangular focal spots, one can similarly find a null or minimal pass frequency to enforce smooth fluence profiles. Additionally, even though FIG. 3 shows MAD0 and MAD1 to be parallel with identical pitch, each of the flat MADs have a slightly different pitch and the bars/slots must be focused to the source due to the diverging x-ray beam.

The last parameter that is important for design is the control parameter $\Delta$, which denotes the relative offset between MAD0 and MAD1. This is the one-dimensional actuation that controls the fluence profile enforced by the MAD filters. In general, this parameter must be part of the design process as well, and is a function of the CT rotation angle and/or table position, which is denoted as $\Delta(\theta)$.

With MAD pitch specified, the remaining parameters: $b_0(x)$, $b_1(x)$, and $\Delta(\theta)$ are sought. These values can be determined analytically using an "endpoint" design to match two desired profiles by considering the minimum and maximum blocking conditions of a dual MAD system. While this approach is attractive due to its closed-form solution, it fails to provide best fit solutions for a wide range of desired fluence patterns. Instead a nonlinear, nonconvex optimization is proposed herein as a part of the present invention.

To facilitate optimization, the dual MAD design is further parameterized using a low-dimensional set of basis functions. For example, rather than have a parameter for every bar width in MAD0, it is assumed that neighboring bar widths vary smoothly as a function of position. Specifically, the parameters are represented with a small set of Fourier coefficients, $c_p(\omega)$ such that $$p(x) = m/(1 + e^{-\hat{p}(x)}) \quad \hat{p}(x) = \mathcal{F}^{-1}[c_p(\omega)]$$

where p(x) is one of $\{b_0(x), b_1(x), \delta(x), \text{ and } \Delta(\theta)\}$. Thus, the optimization will focus on finding the optimal coefficients: $c_{b1}(\omega)$, $c_{b2}(\omega)$, $c_\delta(\omega)$, and $c_\Delta(\omega)$ which are functions of the spatial (or, for D, angular) frequencies selected for the basis set.

To define the optimization objective, a model of the fluence output is constructed, which is a function of the design and actuation values and can be written in terms of the original parameters or vectors of low-dimensional Fourier coefficients:

$$M(b_0(x), b_1(x), \delta(x); \Delta(\theta)) \leftrightarrow M(x, \theta; c_{b1}, c_{b2}, c_\delta, c_\Delta)$$

Note that M is a function of spatial location (e.g., a fluence profile) as well as rotation angle.

Using this model, the following optimization:

$$\left\{\begin{array}{c}\hat{c}_{b1}, \hat{c}_{b2}, \\ \hat{c}_\delta, \hat{c}_\Delta\end{array}\right\} = \text{argmin} \sum_\theta \sum_{x \in P} \left|\frac{t(\theta, x)}{t_0(\theta)} - \frac{M(x, \theta; c_{b1}, c_{b2}, c_\delta, c_\Delta)}{M_0(\theta)}\right|^2$$

where $t(\theta,x)$ denotes desired fluence patterns as a function of rotation angle. The objective is computed as the mean squared error between the desired and modeled fluence patterns over all projections that intersect the phantom (or patient). As such, x-rays passing outside the phantom (e.g. not contributing to dose) will be ignored in the optimization process.

Also note that both the modeled and desired fluence patterns are normalized by $$M_0(\theta) = \sum_x M(x, \theta;.) \text{ and } t_0(\theta) = \sum_x t(\theta, x)$$

respectively. This normalization concentrates the design process on achieving the proper fluence shape. The magnitude of the profile can be adjusted post-design through exposure settings and tube current modulation. While there are many potential desired fluence patterns that one might seek including those that enforce minimum peak variance, combined noise and dose objectives, or maximize task-based detectability, fluence patterns that flatten the signal and homogenize noise in projection data are the focus to show the utility of the present invention.

Covariance Matrix Adaptation Evolution Strategy (CMA-ES) was chosen for the optimization. CMA-ES requires no derivative computations and is well-suited to nonlinear nonconvex optimization since a population of solutions is employed to avoid local optima. The objective function was implemented and the profile modeling function in efficient C++ code including parallelized computation of objective function values (over the population) using OpenMP. The CMA-ES algorithm was initialized to the output of the end-point design process. A population size of 16 was selected and the stopping criteria for optimization was to stop if successive function evaluations differ less than $10^{-12}$ or 10,000 iterations was computed. All the MAD design parameters were constrained to lie between 0 and a single pitch, m, to avoid nonphysical and periodic solutions (e.g. beyond a single cycle of actuation).

Figure 4:
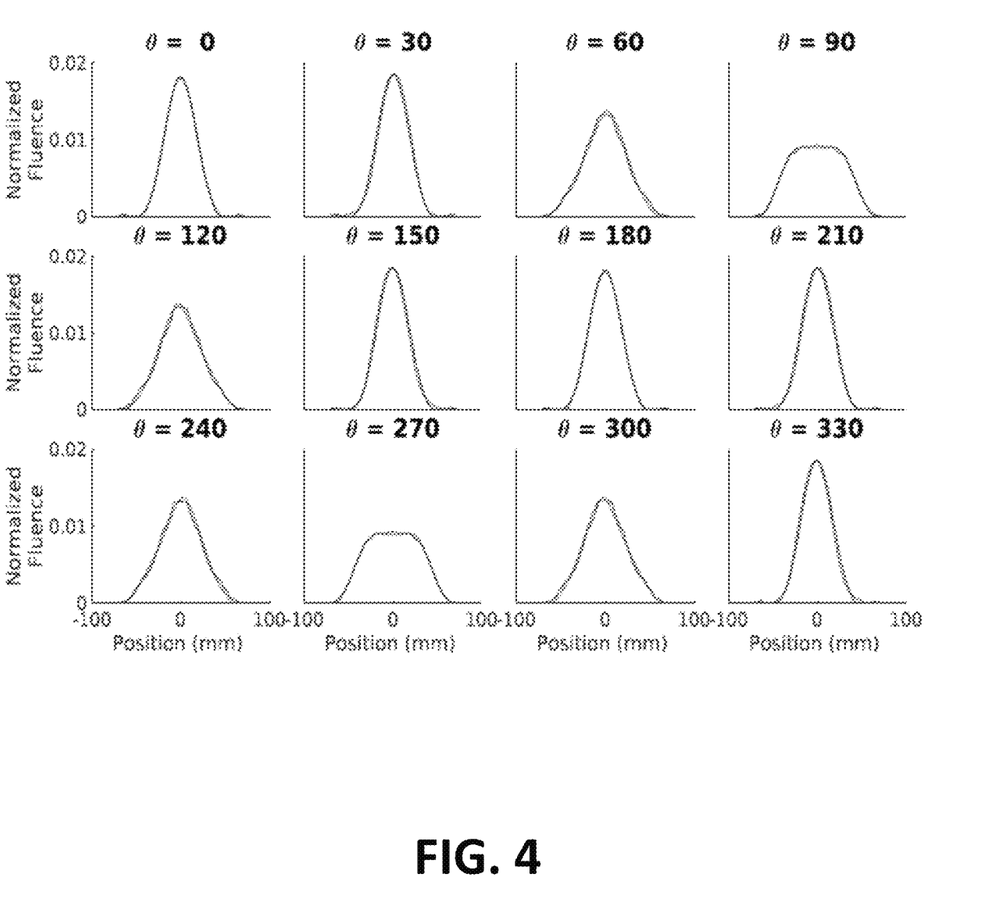
FIG. 4 illustrates graphical views of normalized target fluence patterns at the MAD plane to flatten the fluence through the phantom at the detector plane, and achievable fluence patterns using the dual MAD setup.

To generate desired fluence patterns, the phantom was rotated 360 degrees in steps of 0.5 degrees. The fluence is simulated at the detector plane, and the fluence profile at the MAD plane required to flatten this fluence is computed using the methodology of Section IIB. The MAD parameterization used 8 Fourier coefficients for each MAD feature (4 total), and only symmetric basis functions were employed to enforce symmetric MAD designs. A subset of these target fluence profiles are shown in FIG. 4. FIG. 4 illustrates graphical views of normalized target fluence patterns at the MAD plane to flatten the fluence through the phantom at the detector plane, and achievable fluence patterns using the dual MAD setup. The fluence required is normalized such that the sum is unity. The fluence obtainable with the dual MADs using the CMA-ES optimization is also plotted.

The designed fluence profiles very closely match the desired fluence pattern suggesting that a dual MAD system can match a range of fluence profiles and, in this case, substantially flatten the fluence profiles at the detector for this phantom. For the fluence profiles with a flat top, the achievable CMA-ES profiles show fluctuation on the flat edge. The narrow fluence profiles show slight misalignment error, which is potentially correctable by shifting both MADs together. Such analysis is the topic of ongoing investigations and will likely be important for asymmetric beam profiles (e.g., for miscentered patients, off axis targets, etc.).

Figure 5A:
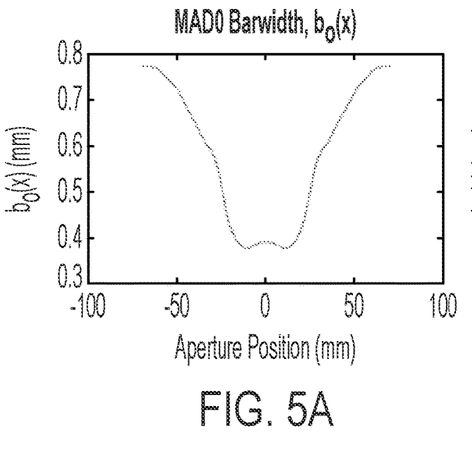
FIGS. 5A-5D illustrate graphical views of solutions to the dual MAD design optimization.
Figure 5B:
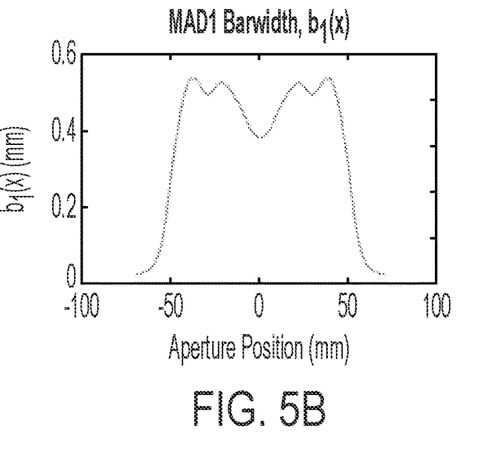
Figure 5C:
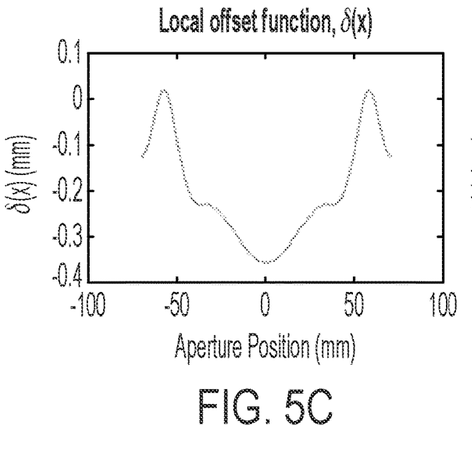
Figure 5D:
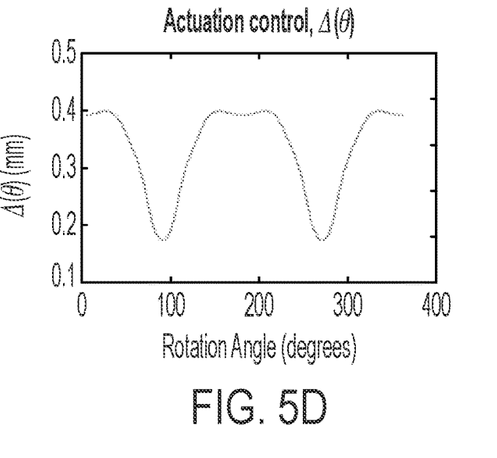

The optimized MAD design parameters are shown in FIGS. 5A-5D. FIGS. 5A-5D illustrate graphical views of solutions to the dual MAD design optimization. FIG. 5A illustrates a bar width function, $b_0(x)$ for MAD0; FIG. 5B illustrates a barwidth function $b_1(x)$ for MAD1; FIG. 5C illustrates a local offset function $\delta(x)$; and FIG. 5D illustrates the actuation control, $\Delta(\theta)$, as a function of rotation angle. Note, because the bar widths are directly proportional to the amount of local blockage and consequently inversely proportional to the local fluence, the effect of the MAD0 filter alone is not unlike a traditional bowtie (e.g. more fluence in the center of the field and less at the edges). The MAD1 design is almost the opposite (when acting alone). The bar widths in both MADs span the range of approximately 50 µm to 800 µm. Such designs are largely within the constraints of modern tungsten sintering technology, though features<100 µm can present some challenges (such constraints can potentially be integrated into the design process). The local offset function, $\delta(x)$, is predominantly negative, meaning that the MAD1 bars are located to the left of the center position in each MAD period.

The actuation control shown in FIG. 5D illustrates that MAD1 is displaced between 0.15 mm to 0.4 mm as the projection angle changes from 0 to 360 degrees. This minimal movement of the MADs causes the large change in the fluence patterns seen in FIG. 4 and can be attributed to the relatively small MAD pitch. From an implementation standpoint, the potential mechanical advantage is the fast switching speed of the MAD fluence profiles as the CT gantry spins around the patient. The smooth profile of the displacement also reduces the acceleration requirements on the actuator. Though not done here, one could integrate specific acceleration limits as part of the optimization.

Figure 6:
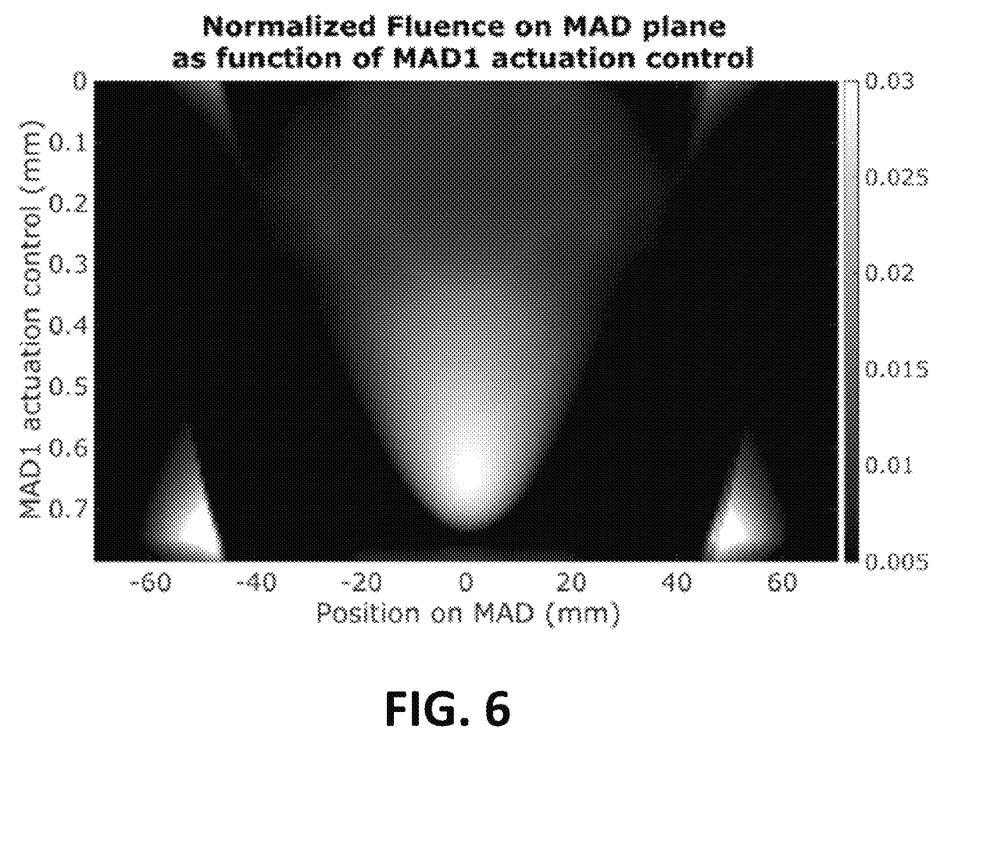
FIG. 6 illustrates a graphical view of post-filtering fluence profiles at the MAD plane with a full range of control actuation (displacements of MAD1 with respect to MAD0).

It is interesting to note that the design of the previous sections only utilizes part of the actuation control range. FIG. 6 shows the full range of fluence patterns achievable as the second MAD is moved with respect to the first MAD within a single MAD pitch (e.g. one cycle). Recall, that for the selected phantom, only fluence profiles between MAD1 displacements of 0.1 to 0.4 were used. FIG. 6 illustrates a graphical view of post-filtering fluence profiles at the MAD plane with a full range of control actuation (displacements of MAD1 with respect to MAD0).

However, from the fluence map, it is clear that much sharper fluence patterns can be obtained by changing the displacement to 0.7 mm. This potentially enables other applications such as region-of-interest fluence modulation and suggests additional design flexibility for larger classes of profiles (e.g. more complex objects, multiple classes, etc.).

Although a variety of fluence patterns have been demonstrated, practical application and fitting to the desired fluence profiles requires proper scaling. This scaling can be achieved through tube current modulation (TCM). Typical Automatic Exposure Control (AEC) seeks to provide a constant fluence at the center of the detector. This strategy was applied for the no filter scenario. For the MAD scenario, the same strategy of providing constant fluence at the central detector pixel was applied, through the Dual MAD and phantom. For comparison between the no filter and MAD filtered scenarios, the total fluence (i.e., the number of simulated photons) incident on the phantom is constant for the two approaches. Specifically, TCM is scaled to enforce a total of 100,000 photons incident on the phantom.

Figure 7:
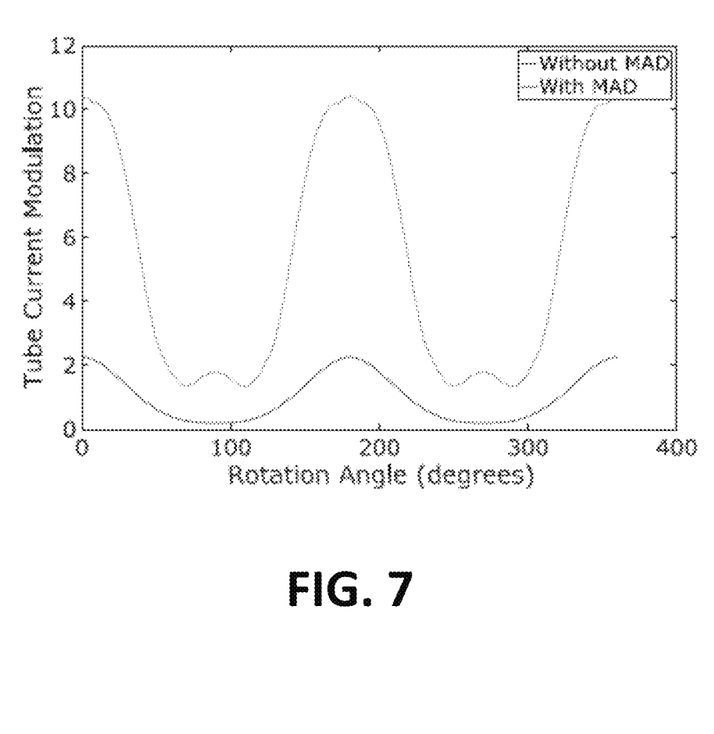
FIG. 7 illustrates a graphical view of tube current modulation with and without MAD filters.

FIG. 7 shows the TCM required to convert the fluence generated by the MADs to the required target fluence. FIG. 7 illustrates a graphical view of tube current modulation with and without MAD filters. The solid line is without MAD and the dashed line is with MAD. Without the MAD filter, the TCM is largest when the path length of X-rays through the phantom is largest. The dual MAD filter has maximum attenuation when the fluence profile is narrow. Therefore, more photons are required at 0 and 180 degrees to flatten the fluence with MAD than at 90 or 270 degrees. The MAD requires higher scaling and modulation to generate the same number of photons incident on the phantom.

Figure 8A:
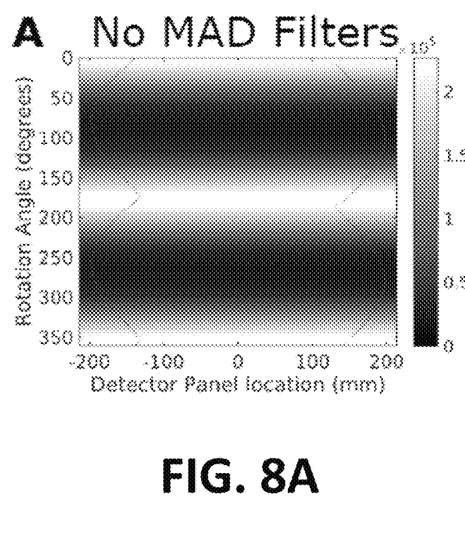
FIGS. 8A and 8B illustrate graphical views of the fluence profiles received at the detector with no phantom scanner.
Figure 8B:
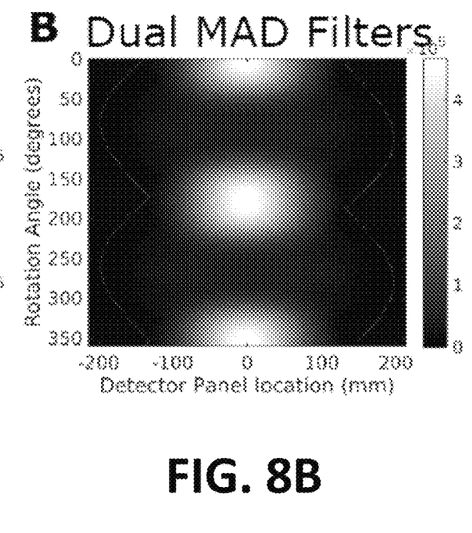
Figure 9A:
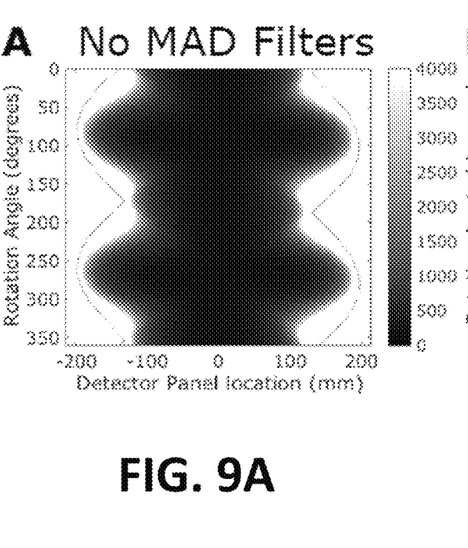
FIGS. 9A and 9B illustrate graphical views of the projection data received at the detector with the phantom in the scanner.
Figure 9B:
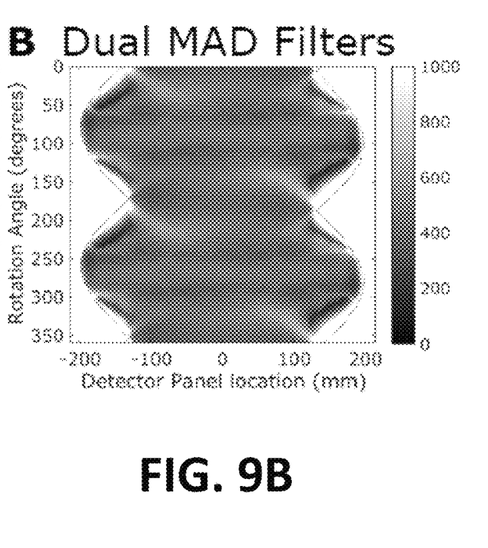

FIGS. 8A and 8B and FIGS. 9A and 9B show the fluence profiles with and without the phantom in the field of view for the no filter and MAD filtered scenarios (TCM is used in both cases). In FIGS. 8A and 8B, the no filter scenario can only modulate the per view number of photons through TCM while the dual MAD filter can customize both the shape and intensity of the beam. In FIGS. 9A and 9B, the post-object fluence is more uniform across object projections (the design goal) than the no filter, TCM-only scenario. FIGS. 8A and 8B illustrate graphical views of the fluence profiles received at the detector with no phantom scanner. FIG. 8A illustrates no filters and AEC, and FIG. 8B illustrates using optimally actuated and designed dual MAD filters and AEC. The space occupied by the phantom is shown by a dotted line. Units are in photons. FIGS. 9A and 9B illustrate graphical views of the projection data received at the detector with the phantom in the scanner. FIG. 9A illustrates using no filters and AEC, and FIG. 9B illustrates using optimally actuated and designed dual MAD filters and AEC. The space occupied by the phantom is shown by a dotted line. Units are in photons.

Figure 10A:
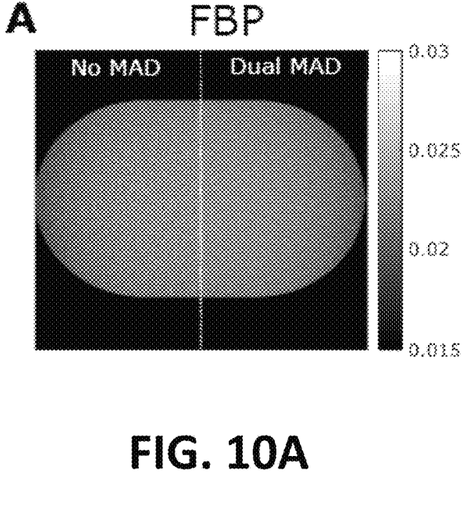
FIG. 10A illustrates an image view of filtered backprojection of a phantom with no MAD filters and dual MAD filters.
Figure 10B:
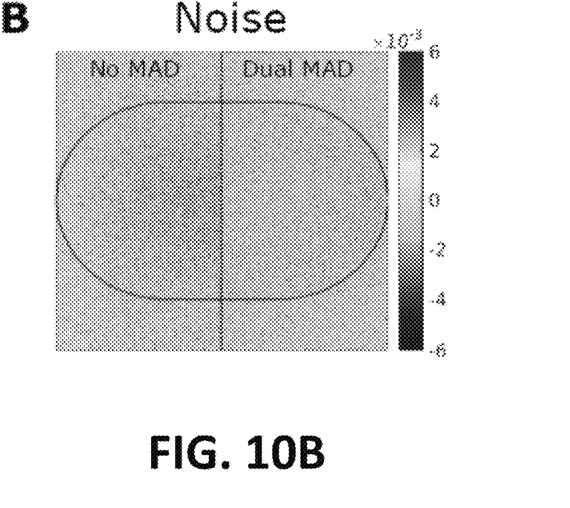
FIG. 10B illustrates noise images with no MAD filter and Dual MAD filter.

With Poisson noise added to the projection data in FIGS. 9A and 9B, filtered backprojection reconstructions were performed for both filtering scenarios. Results are shown in FIGS. 10A and 10B. FIG. 10A illustrates an image view of filtered backprojection of a phantom with no MAD filters and dual MAD filters. FIG. 10B illustrates noise images with no MAD filter and Dual MAD filter. Both methods show approximately the same average noise level (as expected due to an equal number of incident photons). However, much greater noise uniformity exists in the MAD filtered image. This is significant if a minimum noise level is prescribed to obtain sufficient image quality. The TCM-only case will require more incident photons (hence larger dose) to obtain the same minimum noise level over the entire image.

While these initial results suggest that dual MAD filters can successfully achieve a broad class of fluence patterns, this invention can possibly be extended to larger classes of fluence patterns (e.g. different size patients). Similarly, parallel efforts are working to fabricate physical MAD devices and evaluate performance in an experimental CT system.

The present invention can be carried out and/or supported using a computer, non-transitory computer readable medium, or alternately a computing device or non-transitory computer readable medium incorporated into the imaging device. Indeed, any suitable method of calculation known to or conceivable by one of skill in the art could be used. It should also be noted that while specific equations are detailed herein, variations on these equations can also be derived, and this application includes any such equation known to or conceivable by one of skill in the art.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

The computing device can be a special computer designed specifically for this purpose. The computing device can be unique to the present invention and designed specifically to carry out the method of the present invention. Imaging devices generally have a console which is a proprietary master control center of the imager designed specifically to carry out the operations of the imager and receive the imaging data created by the imager. Typically, this console is made up of a specialized computer, custom keyboard, and multiple monitors. There can be two different types of control consoles, one used by the operator and the other used by the physician. The operator's console controls such variables as the thickness of the image, the amount of tube current/voltage, mechanical movement of the patient table and other radiographic technique factors. The physician's viewing console allows viewing of the images without interfering with the normal imager operation. This console is capable of rudimentary image analysis. The operating console computer is a non-generic computer specifically designed by the imager manufacturer for bilateral (input output) communication with the scanner. It is not a standard business or personal computer that can be purchased at a local store. Additionally this console computer carries out communications with the imager through the execution of proprietary custom built software that is designed and written by the imager manufacturer for the computer hardware to specifically operate the hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention. While exemplary embodiments are provided herein, these examples are not meant to be considered limiting. The examples are provided merely as a way to illustrate the present invention. Any suitable implementation of the present invention known to or conceivable by one of skill in the art could also be used.

What is claimed is:

1. A device for beam shaping in imaging comprising:
   two or more multiple aperture devices placed in series between an x-ray source and a subject, wherein each of the multiple aperture devices have a design and each of the multiple aperture devices are configured to have motion relative to others of the multiple aperture devices and each of the multiple aperture devices comprise a plurality of bars having variable widths and spacings;
   wherein the design and the motion of the multiple aperture devices are predetermined to generate a predetermined fluence pattern or the motion of the multiple aperture devices is determined on-the-fly to generate the predetermined fluence pattern; and
   a non-transitory computer readable medium programmed for determining the design of each of the multiple aperture devices to achieve the predetermined fluence pattern, and programmed for control and actuation of relative motion between the two or more multiple aperture devices, wherein control and actuation comprises determining a spacing and position of the multiple aperture devices with respect to one another and with respect to a beam to be shaped in order to generate the predetermined fluence pattern.

2. The device of claim 1 wherein the design and relative motion are chosen using mathematical models or physical models.

3. The device of claim 1 wherein the design and relative motion are chosen using mathematical and physical models.

4. The device of claim 1 wherein the predetermined fluence pattern is based on a single target object.

5. The device of claim 1 wherein the predetermine fluence pattern is based on a group of target objects.

6. The device of claim 1 wherein each of the two or more multiple aperture devices comprises bars.

7. The device of claim 6 further comprising design characteristics taking a form of thickness of each bar.

8. The device of claim 6 further comprising design characteristics taking a form of position of each bar relative to one another.

9. The device of claim 6 further comprising design characteristics taking a form of a frequency of the bars.

10. A method for beam shaping in imaging comprising:
    placing two or more multiple aperture devices in series between an x-ray source and a subject, wherein each of the multiple aperture devices have a design and each of the multiple aperture devices are configured to have motion relative to others of the multiple aperture devices and each of the multiple aperture devices comprise a plurality of bars having variable widths and spacings;
    generating a fluence pattern; and
    using a non-transitory computer readable medium programmed for determining the design of each of the multiple aperture devices to achieve a predetermined fluence pattern based on the fluence pattern that is generated, and programmed for control and actuation of relative motion between the two or more multiple aperture devices, wherein control and actuation comprises determining a spacing and position of the multiple aperture devices with respect to one another and with respect to a beam to be shaped from the x-ray source in order to generate the predetermined fluence pattern.

11. The method of claim 10 further comprising predetermining the design and the motion of the two or more multiple aperture devices to generate the predetermined fluence pattern.

12. The method of claim 10 further comprising determining the motion of the two or more multiple aperture devices on-the-fly to generate a fluence pattern.

13. The method of claim 10 further comprising programming the design and relative motion with one chosen from a group consisting of using mathematical models, physical models, or a combination of the two.

14. The method of claim 10 further comprising basing the predetermined fluence pattern on a single target object.

15. The method of claim 10 further comprising basing the predetermine fluence pattern on a group of target objects.

16. The method of claim 10 further comprising the two or more multiple aperture device comprising bars.

17. The method of claim 10 further comprising design characteristics taking a form of thickness of each bar.

18. The method of claim 10 further comprising design characteristics taking a form of position of each bar relative to one another.

19. The method of claim 10 further comprising design characteristics taking a form of the frequency of the bars.

20. The device of claim 1, wherein a spacing between the plurality of bars are arranged to minimize high-frequency patterns at a detector.

* * * * *